United States Patent [19]
Kennedy et al.

[11] Patent Number: 4,793,996
[45] Date of Patent: Dec. 27, 1988

[54] METHOD OF MAKING SOYBEAN EXTRACT INHIBITOR

[75] Inventors: Ann R. Kennedy, 145 Fuller St., West Newton, Mass. 02165; Walter Troll, Brooklyn, N.Y.; Jonathan Yavelow, Lawrenceville, N.J.

[73] Assignee: Ann R. Kennedy, Wynnewood, Pa.

[21] Appl. No.: 912,190

[22] Filed: Sep. 25, 1986

Related U.S. Application Data

[63] Continuation of Ser. No. 671,229, Nov. 14, 1984, abandoned.

[51] Int. Cl.$^4$ .............................................. A61K 35/00
[52] U.S. Cl. .............................. 424/195.1; 260/412.4; 426/430; 426/481; 426/634; 426/655
[58] Field of Search ............... 426/634, 630, 655, 425, 426/430, 481; 260/412.4; 424/195.1

[56] References Cited

U.S. PATENT DOCUMENTS

| | | | |
|---|---|---|---|
| 3,408,374 | 10/1968 | Cavanagh et al. | 260/412.4 |
| 3,520,868 | 7/1970 | Henderson et al. | 426/430 X |
| 4,008,210 | 2/1977 | Steele et al. | 426/430 X |
| 4,435,438 | 3/1984 | Lehnhardt et al. | 426/430 X |

OTHER PUBLICATIONS

Markley, K. S., Soybeans and Soybean Products, vol. 1, Interscience Publ., Inc., N.Y., 1950, pp. 356–358.
Perlmann et al., Meth. Enzymol., 19, 860, (1970).
Yavelow et al., Cancer Res. (Suppl.), 43, 2454s, (1983).
Circle, Soybeans and Soybean Products, Markley, Ed., Interscience Publ., Inc., N.Y., pp. 356–358, (1950).
Hwang et al., Biochim. Biophys. Acta, 495, 369, (1977).
Yavelow et al., Proc. Nat. Acad. Sci., U.S.A., 82, 5395, (1985).
Kennedy et al., Nature, 276, 825, (1978).
Kennedy et al., Cancer Res., 41, 2103, (1981).
Kennedy et al., Proc. Nat. Acad. Sci., U.S.A., 81, 1827, (1984).

Primary Examiner—Steven Weinstein
Assistant Examiner—Celine T. Callahan
Attorney, Agent, or Firm—Robbins & Laramie

[57] ABSTRACT

In the process of preparing a soybean extract exhibiting inhibition of malignant transformation of cells which comprises defatting soybeans and extracting the inhibitor from the defatted soybeans, the step of defatting the soybeans by bringing them into contact with acetone provides an edible extract of increased effectiveness.

16 Claims, No Drawings

METHOD OF MAKING SOYBEAN EXTRACT INHIBITOR

The invention described herein was made with U.S. Government support and the Government has certain rights therein.

This application is a continuation of application Ser. No. 671,229, filed Nov. 14, 1984, now abandoned.

This invention relates to the preparation of a soybean extract having improved effectiveness as an inhibitor of malignant transformation of cells and pertains more specifically to the use of acetone in the defatting step.

It has long been known that an inhibitor of the malignant transformation of cells, known as the Bowman-Birk inhibitor, as described by Yavelow et al., Cancer Research (Suppl.), Vol. 43, 2454s–2459s (1983) can be prepared by defatting soybeans with ether, followed by extraction of the defatted soybeans, as described in Perlmann et al., Methods in Enzymology, Vol. 19, 860–861 (1970). In practice, it is unnecessary to carry out a procedure involving complete purification of the extract to the point where the product contains only a single protein as the active inhibitor, but instead it has been found economical to stop the purification procedure at the point where a crude inhibitor extract is obtained. This crude extract is itself edible and can be used as an inhibitor of malignant transformation of cells, for example by oral ingestion.

It has now been found that in the process of preparing a crude soybean extract containing an inhibitor of malignant transformation of cells which comprises defatting soybeans and extracting said inhibitor from said defatted soybeans, the improvement which comprises defatting said soybeans by bringing them into contact with at least an equal weight of acetone produces a crude inhibitor extract having greatly increased effectiveness.

In the process of the present invention, soybeans, preferably in finely-divided form such as soybean meal, are defatted by bringing them into contact with at least an equal weight of acetone, after which the defatted soybeans are subjected to the usual alcoholic extraction procedure, acetone precipitation, dialysis of an aqueous solution, and drying by lyophilization or ultrafiltration. The defatting step is preferably carried out at a temperature from room temperature up to the boiling point of acetone and may conveniently be carried out at reflux temperature and at atmospheric pressure. Although higher pressures may be employed, they are not necessary. While as little as an amount of acetone equal to the weight of the soybeans can be used, more rapid and more complete defatting is achieved by using a weight of acetone from 5 to 10 times that of the soybeans.

The subsequent extraction of the inhibitor from the defatted soybeans can be conducted in the usual manner by extraction with ethyl alcohol to form a solution, precipitation of the crude inhibitor from the solution by the addition of acetone, dissolution of the precipitate in water followed by dialysis against water, and ultrafiltration or lyophilization to provide a concentrate, preferably in dry solid form.

The following specific example is intended to illustrate more fully the nature of the invention without acting as a limitation upon its scope.

EXAMPLE

Approximately 600 grams of commercially available soybean meal (Sigma Chemical Co., 1% lipid content) was mixed with 6 liters of acetone and stirred for ½ hour at room temperature, then filtered. This procedure ws repeated three times and then the defatted soybean meal was dried at room temperature. The dried material was then added to 6 liters of 60% aqueous ethanol maintained at 60° C. The mixture was stirred 1 hr. at 55°–60° C., cooled to room temperature and filtered on a Buchner funnel, discarding the precipitate. The pH of the filtrate was adjusted to 5.3 with 1M hydrochloric acid, then mixed with twice its volume of acetone to precipitate the crude active agent, which was separated by filtration, dried at room temperature, then dissolved in 500 ml of water. The aqueous solution was dialyzed against water at 5° C. using Spectrapor No. 3 membrane tubing for at least 3 days with numerous changes of water. The resulting precipitate was separated by centrifugation and discarded. The remaining supernatant was lyophilized to a dry powder.

The effectiveness of the dry powder was compared to that of an inhibitor prepared by the same procedure described above except that ethyl ether was employed in the defatting step instead of acetone. The test procedure was a conventional tissue culture assay as described by Reznikoff et al., Cancer Res., Vol. 33, 3231–3238, and 3239–3249 (1973) involving the C3H/10T ½ cell transformation system. Stock cultures of the C3H mouse embryo cells were maintained in 60-mm Petri dishes and were passed by subculturing at a 1:20 dilution every 7 days. The cells used were in passages 9 to 14. They were grown in a humidified 5% carbon dioxide atmosphere at 37° C. in Eagle's basal medium supplemented with 10% heat-inactivated fetal calf serum and gentamycin. The concentration of serum was reduced to 5% on day 10 and was maintained at this concentration throughout the remainder of 6-week assay period. All dishes used for the transformation assay contained approximately 300 viable cells per dish. Type 2 and 3 foci were scored as transformants. Each culture was exposed to 600 rads of X-rays, followed immediately by the addition of varying amounts of the crude inhibitor extract prepared in accordance with the foregoing example of the invention, or by the addition of crude inhibitor extract made by the same procedure except that ether was used in the defatting step instead of acetone. The results are shown in the following table:

TABLE

| Inhibitor Added, μg/ml | | Fraction of dishes containing transformed foci, Types 2 and 3 |
|---|---|---|
| Made with acetone | 300 | 4/31 = 0.12 |
| | 100 | 1/18 = 0.06 |
| | 10 | 2/20 = 0.10 |
| | 1 | 5/40 = 0.13 |
| | 0.1 | 7/20 = 0.35 |
| | 0.01 | 4/17 = 0.24 |
| | 0.001 | 10/18 = 0.56 |
| None | — | 28/62 = 0.45 |
| Made with ether | 300 | 8/14 = 0.57 |
| None | — | 10/17 = 0.59 |

As is clear from the foregoing results, crude inhibitor extract made in accordance with the present invention is at least several orders of magnitude more effective in inhibiting malignant transformation of cells than is crude inhibitor extract made using diethyl ether in the defatting step. The crude extract may be further purified if desired by any of the conventional procedures such as chromatography and further dialysis.

What is claimed is:

1. A process for preparing a Bowman-Birk inhibitor from soybeans which comprises the steps of:
   (a) treating soybeans with at least an equal weight of acetone by mixing said soybeans in a dry, finely-divided form with said acetone for a sufficient time and at a sufficient temperature to provide said inhibitor with the capability of inhibiting malignant transformation of cells;
   (b) extracting the treated soybeans with ethyl alcohol or aqueous ethyl alcohol for a sufficient time and at a sufficient temperature to form a solution containing said inhibitor;
   (c) separating residual solids from said solution; and
   (d) precipitating the inhibitor from said solution by mixing the solution with acetone, whereby an inhibitor is obtained which is capable of inhibiting malignant transformation of C3H mouse embryo cells.

2. The process of claim 1 wherein step (a) is carried out at a temperature from room temperature to the boiling point of acetone.

3. The process of claim 2 wherein the weight of acetone in step (a) is from about five times to about ten times the weight of the soybeans.

4. The process of claim 3 which further comprises purifying the acetone-precipitated inhibitor.

5. The process of claim 4 wherein said soybeans have been defatted prior to the treatment with acetone in step (a).

6. The process of claim 3 wherein said soybeans have been defatted prior to the treatment with acetone in step (a).

7. The process of claim 2 which further comprises purifying the acetone-precipitated inhibitor.

8. The process of claim 7 wherein said soybeans have been defatted prior to the treatment with acetone in step (a).

9. The process of claim 2 wherein said soybeans have been defatted prior to the treatment with acetone in step (a).

10. The process of claim 1 wherein the weight of acetone in step (a) is from about five times to about ten times the weight of the soybeans.

11. The process of claim 10 which further comprises purifying the acetone-precipitated inhibitor.

12. The process of claim 11 wherein said soybeans have been defatted prior to the treatment with acetone in step (a).

13. The process of claim 10 wherein said soybeans have been defatted prior to the treatment with acetone in step (a).

14. The process of claim 1 which further comprises purifying the acetone-precipitated inhibitor.

15. The process of claim 14 wherein said soybeans have been defatted prior to the treatment with acetone in step (a).

16. The process of claim 1 wherein said soybeans have been defatted prior to the treatment with acetone in step (a).

* * * * *